(12) United States Patent
Mayer et al.

(10) Patent No.: US 8,658,429 B1
(45) Date of Patent: Feb. 25, 2014

(54) PHOTOLUMINESCENT OXYGEN PROBE TACK

(75) Inventors: Daniel W. Mayer, Wyoming, MN (US); John Eastman, Rogers, MN (US)

(73) Assignee: Mocon, Inc., Minneapolis, MN (US)

( * ) Notice: Subject to any disclaimer, the term of this patent is extended or adjusted under 35 U.S.C. 154(b) by 31 days.

(21) Appl. No.: 13/567,362

(22) Filed: Aug. 6, 2012

(51) Int. Cl.
G01N 33/00 (2006.01)
G01N 33/02 (2006.01)
G01N 21/64 (2006.01)
G01N 21/76 (2006.01)

(52) U.S. Cl.
USPC ............ 436/138; 436/20; 436/127; 436/136; 436/164; 436/167; 436/172; 436/181; 422/52; 422/400; 422/416; 422/82.05; 422/82.08; 422/83; 422/88; 411/439; 411/487

(58) Field of Classification Search
USPC ........... 436/20, 127, 136, 138, 164, 167, 169, 436/172, 181; 422/52, 400, 408, 410, 416, 422/420, 68.1, 82.05, 82.08, 83, 88; 411/439, 487; 470/47
See application file for complete search history.

(56) References Cited

U.S. PATENT DOCUMENTS

| | | | |
|---|---|---|---|
| 3,138,937 A | 6/1964 | Parkinson et al. |
| 4,476,870 A | 10/1984 | Peterson et al. |
| 4,784,811 A | 11/1988 | Hirschfeld |
| 4,810,655 A | 3/1989 | Khalil et al. |
| 4,947,850 A | 8/1990 | Vanderkooi et al. |
| 5,190,729 A | 3/1993 | Hauenstein et al. |
| 5,328,823 A | 7/1994 | Spencer et al. |
| 5,333,609 A | 8/1994 | Bedingham et al. |
| 5,382,163 A | 1/1995 | Putnam |
| 5,407,829 A | 4/1995 | Wolfbeis et al. |
| 5,695,640 A | 12/1997 | Tseng |
| 5,718,842 A | 2/1998 | Papkovsky et al. |
| 5,837,865 A | 11/1998 | Vinogradov et al. |
| 6,074,607 A | 6/2000 | Slovacek et al. |
| 6,153,701 A | 11/2000 | Potnis et al. |
| 6,165,741 A | 12/2000 | Wilson et al. |
| 6,266,211 B1 | 7/2001 | Thomas, III et al. |
| 6,328,932 B1 | 12/2001 | Carter et al. |

(Continued)

FOREIGN PATENT DOCUMENTS

| | | |
|---|---|---|
| WO | 9219150 A1 | 11/1992 |
| WO | 2006095191 A1 | 9/2006 |
| WO | 2007120637 A2 | 10/2007 |

OTHER PUBLICATIONS

Lee, Sang-Kyung et al., "Photoluminescent Oxygen Sensing on a Specific Surface Area Using Phosphorescence Quenching of Pt-Pophyrin", Analytical Sciences, Department of Bioengineering, Tokyo Institute of Technology, pp. 535-540, Aug. 1997, vol. 13.

(Continued)

Primary Examiner — Maureen Wallenhorst
(74) Attorney, Agent, or Firm — Sherrill Law Offices, PLLC

(57) ABSTRACT

A photoluminescent oxygen probe including a tack with a layer of a pressure-sensitive adhesive and an oxygen-sensitive photoluminescent element on the underside of the head. The probe is effective for sensing oxygen concentration within an enclosed space by puncturing the container defining the enclosed space the with the probe's shank and adhering the underside of the probe's head to the container so as to sealingly surround the puncture, thereby placing the oxygen-sensitive photoluminescent dye on the underside of the probe's head into sensible communication with the enclosed space through the puncture hole.

15 Claims, 4 Drawing Sheets

(56) References Cited

U.S. PATENT DOCUMENTS

| | | | |
|---|---|---|---|
| 6,362,175 | B1 | 3/2002 | Vinogradov et al. |
| 6,379,969 | B1 | 4/2002 | Mauze et al. |
| 6,395,555 | B1 | 5/2002 | Wilson et al. |
| 6,689,438 | B2 | 2/2004 | Kennedy et al. |
| 7,138,270 | B2 | 11/2006 | Papkovsky et al. |
| 7,368,153 | B2 | 5/2008 | Barmore et al. |
| 7,534,615 | B2 | 5/2009 | Havens |
| 7,569,395 | B2 | 8/2009 | Havens et al. |
| 7,642,250 | B2 | 1/2010 | Williams |
| 8,173,438 | B1 * | 5/2012 | Putnam et al. ............... 436/138 |
| 2003/0050543 | A1 | 3/2003 | Hartmann |
| 2005/0159497 | A1 | 7/2005 | Gauthier et al. |
| 2006/0002822 | A1 | 1/2006 | Papkovsky et al. |
| 2006/0201830 | A1 * | 9/2006 | Schoen et al. ............ 206/308.1 |
| 2007/0041011 | A1 | 2/2007 | Hayden et al. |
| 2007/0072825 | A1 | 3/2007 | Williams |
| 2007/0212789 | A1 | 9/2007 | Havens et al. |
| 2007/0212792 | A1 | 9/2007 | Havens et al. |
| 2008/0051646 | A1 | 2/2008 | Papkovsky et al. |
| 2008/0117418 | A1 | 5/2008 | Claps et al. |
| 2008/0148817 | A1 | 6/2008 | Miller et al. |
| 2008/0190172 | A1 | 8/2008 | Jones |
| 2008/0199360 | A1 | 8/2008 | Shahriari |
| 2008/0215254 | A1 | 9/2008 | Leiner et al. |
| 2008/0242870 | A1 | 10/2008 | Meador et al. |
| 2009/0028756 | A1 | 1/2009 | Shahriari |
| 2009/0029402 | A1 | 1/2009 | Papkovsky |
| 2009/0075321 | A1 | 3/2009 | Obeid et al. |
| 2009/0130700 | A1 | 5/2009 | Ince et al. |
| 2010/0116017 | A1 * | 5/2010 | Mayer et al. ................. 73/1.06 |
| 2010/0209693 | A1 | 8/2010 | Hester et al. |
| 2012/0129268 | A1 * | 5/2012 | Mayer ......................... 436/138 |

OTHER PUBLICATIONS

Papkovsky, D. et al., "Phosphorescent Sensor Approach for Non-Destructive Measurement of Oxygen in Packaged Foods: Optimisation of Disposable Oxygen sensors and Their Characterization Over a Wide Temperature Range". Department of Biochemistry, National University of Ireland, Analytical Letters, 33 (9), pp. 1755-1777, Feb. 22, 2000.

Austin, J. P. et al., "Opto-electronic systems for addressing Ru Oxygen Sensors: Their Design Optimization and Calibration Process", Invited Paper, Optoelectronics Research Centre, University of Southampton, Southampton S017 IBJ, Oct. 30, 2001.

Eaton, K. et al., "Effect of Humidity on the Response Characteristics of Luminescent PtOEP Thin Film Optical Oxygen Sensors", Sensors and Actuators B, Elseiver Science B. V. , vol. 82, pp. 94-104, May 18, 2001.

De Francisci, M. et al., "Real-Time Estimation of Oxigen Concentration in Micro-Hemo-Vessels", Proceedings of the 26th Annual International Conference of the IEEE EMBS, San Francisco, CA, USA, pp. 2231-2234, Sep. 1-5, 2004.

Technical Manual, Grafted Separators, "Freudenberg Grafted Products", Sep. 2006, pp. 1-32.

* cited by examiner

PHOTOLUMINESCENT OXYGEN PROBE TACK

BACKGROUND

Solid-state polymeric materials based on oxygen-sensitive photoluminescent dyes are widely used as optical oxygen probes. See, for example United States Published Patent Applications 2009/0029402, 2008/8242870, 2008/215254, 2008/199360, 2008/190172, 2008/148817, 2008/146460, 2008/117418, 2008/0051646, 2006/0002822 and U.S. Pat. Nos. 7,569,395, 7,534,615, 7,368,153, 7,138,270, 6,689,438, 5,718,842, 4,810,655, and 4,476,870. Such optical probes are available from a number of suppliers, including Presens Precision Sensing, GmbH of Regensburg, Germany, Oxysense of Dallas, Tex., United States, and Luxcel Biosciences, Ltd of Cork, Ireland.

Such probes may be interrogated through many common packaging materials and therefore allow nondestructive measurement of the oxygen concentration within an enclosure by simply incorporating a probe within the packaging, typically adhered to the inside surface of the cover. Unfortunately, there are certain applications where incorporation of such a probe into the packaging is not acceptable—such as packages made from materials that interfere with interrogation of the probe (e.g., opaque and metalized films), packages in which the presence of such a probe inside the packaging may be mistakenly perceived by consumers as an undesired contamination of the packaged product, or packages whose per package value or profit margin cannot accommodate the cost of incorporating a probe into every package or tracking those containing a probe when only select packages include a probe.

Hence, a need exists for an inexpensive disposable probe that can be systematically employed in accordance with a quality control program to quickly and accurately inspect the oxygen concentration within indiscriminately selected packages.

SUMMARY OF THE INVENTION

A first aspect of the invention is a photoluminescent oxygen probe comprising (a) a tack with a head and a shank extending longitudinally from an underside of the head, (b) a layer of a pressure-sensitive adhesive on the underside of the head, and (c) an oxygen-sensitive photoluminescent element on the underside of the head. The oxygen-sensitive photoluminescent element is preferably comprised of a photoluminescent dye embedded within an oxygen-permeable hydrophobic polymer carrier.

A second aspect of the invention is a method for measuring oxygen concentration within a space enclosed by a structure employing an oxygen-sensitive probe according to the first aspect of the invention. The method includes the steps of (A) obtaining a photoluminescent oxygen probe according to the first aspect of the invention, (B) puncturing the structure with the probe's shank, (C) adhering the underside of the probe's head to an exterior surface of the container so as to sealingly surround the puncture, thereby placing the oxygen-sensitive photoluminescent dye on the underside of the probe's head into sensible communication with the enclosed space through the puncture, (D) allowing the oxygen concentration in sensible communication with the layer of oxygen-sensitive photoluminescent dye to equilibrate with the oxygen concentration within the enclosed space, and (E) ascertaining an oxygen concentration within the enclosed space by: (i) exposing the oxygen-sensitive photoluminescent dye on the underside of the probe's head to excitation radiation through the probe's head, (ii) measuring radiation emitted by the excited oxygen-sensitive photoluminescent dye, and (iii) converting the measured emission to an oxygen concentration based upon a known conversion algorithm.

A third aspect of the invention is a method for monitoring changes in oxygen concentration within an enclosed space employing an oxygen-sensitive probe according to the first aspect of the invention. The method includes the steps of (A) obtaining a photoluminescent oxygen probe according to the first aspect of the invention, (B) puncturing the structure with the probe's shank, (C) adhering the underside of the probe's head to an exterior surface of the container so as to sealingly surround the puncture, thereby placing the oxygen-sensitive photoluminescent dye on the underside of the probe's head into sensible communication with the enclosed space through the puncture, (D) allowing the oxygen concentration in sensible communication with the layer of oxygen-sensitive photoluminescent dye to equilibrate with the oxygen concentration within the enclosed space, (E) ascertaining an oxygen concentration within the enclosed space over time by: (i) repeatedly exposing the equilibrated oxygen-sensitive photoluminescent dye on the underside of the probe's head to excitation radiation through the probe's head over time, (ii) measuring radiation emitted by the excited equilibrated oxygen-sensitive photoluminescent dye after at least some of the exposures, (iii) measuring passage of time during the repeated excitation exposures and emission measurements, and (iv) converting at least some of the measured emissions to an oxygen concentration based upon a known conversion algorithm, and (F) reporting at least one of (i) at least two ascertained oxygen concentrations and the time interval between those reported concentrations, and (ii) a rate of change in oxygen concentration within the enclosed space calculated from data obtained in step (E).

DETAILED DESCRIPTION OF A PREFERRED EMBODIMENT

Definitions

As used herein, including the claims, the term "foodstuff" means any substance suitable for being eaten or drunk by animals, including humans, for nutrition or pleasure, or used as an ingredient in such a substance.

As used herein, including the claims, the phrase "oxygen impermeable" means a material that has an oxygen transmission rate of less than 0.1 cm$^3$/m$^2$ day when measured in accordance with ASTM D 3985.

NOMENCLATURE

| | |
|---|---|
| 10 | Oxygen Probe |
| 20 | Tack |
| 21 | Head of Tack |
| 21a | Topside of Head |
| 21b | Underside of Head |
| 22 | Shank of Tack |
| 22b | Distal End of Shank |
| 30 | Oxygen-Sensitive Photoluminescent Element |
| 31 | Support Structure |
| 32 | Polymer Carrier |
| 33 | Oxygen-Sensitive Photoluminescent Dye |
| 34 | Coated Individual Strand of Support Structure |
| 39 | Peripheral Edge of Oxygen-Sensitive Photoluminescent Element |
| 40 | Pressure Sensitive Adhesive Layer |
| 49 | Peripheral Edge of Pressure Sensitive Adhesive Layer |
| 50 | Peripheral Margin |
| 60 | Release Liner |
| 61 | Tab on Release Liner |
| 70 | Label |
| F | Foodstuff |
| P | Hermetically Sealed Packaging |
| S | Retention Chamber or Space |

DESCRIPTION

Construction and Theory of Operation

Figure 1:
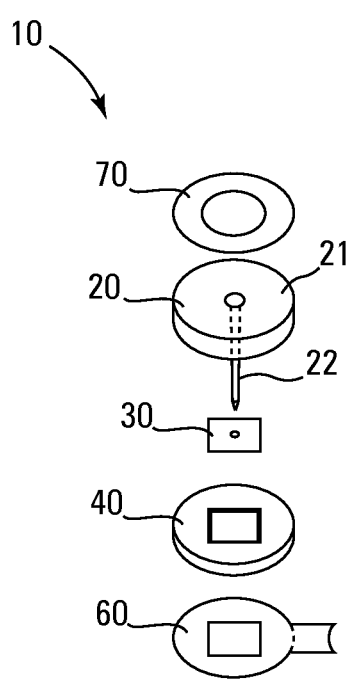
FIG. 1 is an exploded perspective view of one embodiment of the invention.
Figure 2:
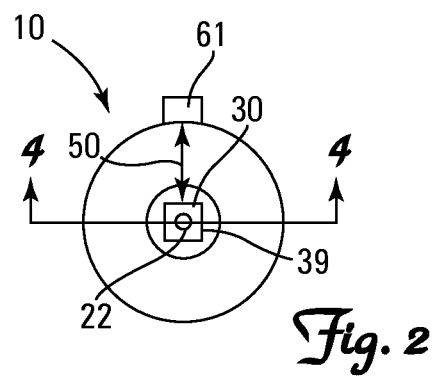
FIG. 2 is a top view of the invention depicted in FIG. 1.
Figure 3:
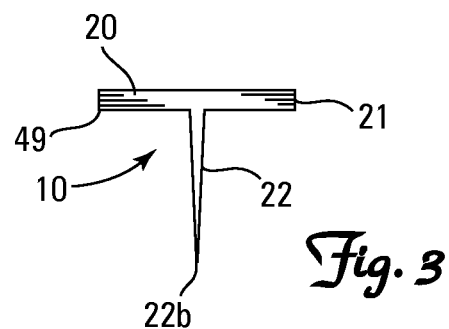
FIG. 3 is a side view of the invention depicted in FIG. 1.
Figure 7:
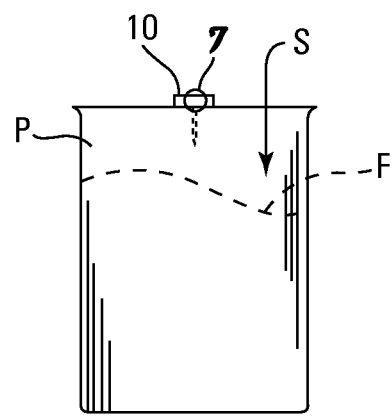
FIG. 7 is a side view of the invention depicted in FIG. 1 applied to a package.

Referring generally to FIG. 7, the invention is an oxygen-sensitive probe or sensor 10 useful for optically measuring oxygen concentration within an enclosed space S, such as the retention chamber S of a hermetically sealed package P containing a foodstuff F. Referring generally to FIGS. 1, 2 and 3, the probe 10 includes a tack 20, oxygen-sensitive photoluminescent element 30 and layer of a pressure-sensitive adhesive 40.

The tack 20 has a head 21 and a shank 22. The head 21 should be transparent or translucent to radiation at the excitation and emission wavelengths of the photoluminescent element 30. Suitable materials include specifically, but not exclusively, glass and various polymers such as poly(methyl methacrylate) and clear vinyl. The shank 22 extends longitudinally from the underside 21b of the head 21. The distal end 22b of the shank 22 forms a sharp suitable for piercing typical packaging materials such as mylar films, polyethylene and polypropylene containers, polyvinyl chloride bottles, etc.

For typical applications, the head 21 preferably has a diameter of about 6 to 20 mm, most preferably about 10 to 15 mm, and the shank 22 preferably has a longitudinal length of about 6 to 20 mm, most preferably about 10 to 15 mm. A head 21 with a diameter smaller than about 6 mm is difficult to manufacture and awkward to use, while a diameter greater than about 20 mm increases the expense of the tack 20 without a concomitant improvement in handling or performance. A shank 22 with a length smaller than about 6 mm hinders the ability of the tack 20 to effectively penetrate and pierce through packages or containers P, while a length greater than about 20 mm increases the expense of the tack 20 without a concomitant improvement in handling or performance.

Figure 4:
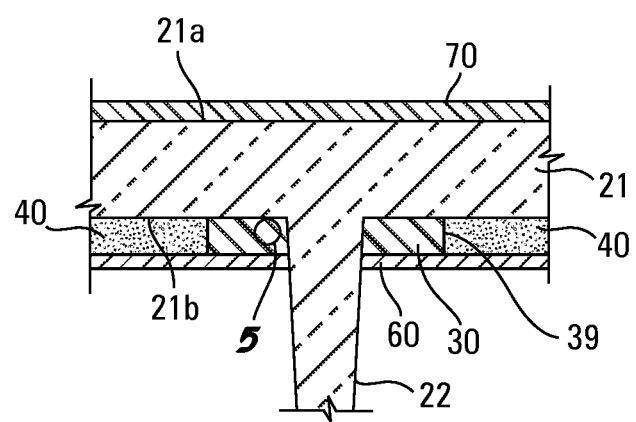
FIG. 4 is a partial cross-sectional side view of the invention depicted in FIG. 1 taken along line 4-4 with the thickness of each layer grossly enlarged to facilitate viewing of the individual layers.

Referring to FIG. 4, both the oxygen-sensitive photoluminescent element 30 and the layer of pressure-sensitive adhesive 40 are positioned on the underside 21b of the head 21 of the tack 20.

Figure 5:
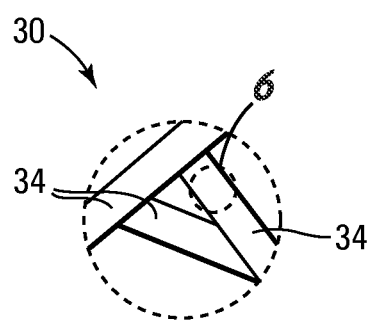
FIG. 5 is a microscopically enlarged view of a portion of the oxygen-sensitive photoluminescent element depicted in FIG. 4 to facilitate viewing of the individual discrete strands of the element.
Figure 6:
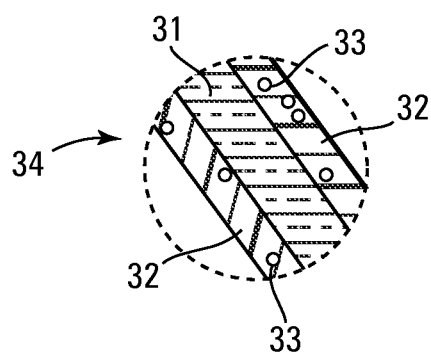
FIG. 6 is a further microscopically enlarged cross-sectional view of one of the strands of the oxygen-sensitive photoluminescent element depicted in FIG. 5 to facilitate viewing of the individual discrete components of the element.

Referring to FIGS. 5 and 6, the oxygen-sensitive photoluminescent element 30 includes an oxygen-sensitive photoluminescent dye 33, preferably embedded within an oxygen-permeable polymer carrier 32, and coated onto a support structure 31.

The oxygen-sensitive photoluminescent dye 33 may be selected from any of the well-known oxygen sensitive photoluminescent dyes 33. One of routine skill in the art is capable of selecting a suitable dye 33 based upon the intended use of the probe 10. A nonexhaustive list of suitable oxygen sensitive photoluminescent dyes 33 includes specifically, but not exclusively, ruthenium(II)-bipyridyl and ruthenium(II)-diphenylphenanothroline complexes, porphyrin-ketones such as platinum(II)-octaethylporphine-ketone, platinum (II)-porphyrin such as platinum(II)-tetrakis(pentafluorophenyl)porphine, palladium(II)-porphyrin such as palladium(II)-tetrakis(pentafluorophenyl)porphine, phosphorescent metallocomplexes of tetrabenzoporphyrins, chlorins, azaporphyrins, and long-decay luminescent complexes of iridium (III) or osmium(II).

Typically and preferably, the oxygen-sensitive photoluminescent dye 33 is compounded with a suitable oxygen-permeable and hydrophobic polymeric carrier 32. Again, one of routine skill in the art is capable of selecting a suitable carrier 32 based upon the intended use of the probe 10 and the selected dye 33. A nonexhaustive list of suitable polymers for use as the oxygen-permeable hydrophobic carrier 32 includes specifically, but not exclusively, polystryrene, polycarbonate, polysulfone, polyvinyl chloride and some co-polymers.

The support structure 31 should be constructed from a material capable of providing sufficient structural integrity to the oxygen-sensitive photoluminescent element 30. The material should also be transparent or translucent to radiation at the excitation and emission wavelengths of the dye 33 in the photoluminescent element 30. Suitable materials include specifically, but not exclusively, glass, spunbond glass fibers and polymeric films such as PET, Nylon, PVDC (Saran), etc.

Referring generally to FIGS. 1 and 4, the probe 10 includes a layer of a pressure sensitive adhesive 40 on underside 21b of the head 21 of the tack 20—the same side as the photoluminescent element 30—for adhering the probe 10 to the surface (unnumbered) of a container or package P defining an enclosed space or retention chamber S whose oxygen concentration is to be measured. The adhesive 40 may but preferably does not cover the photoluminescent element 30.

Figure 8:
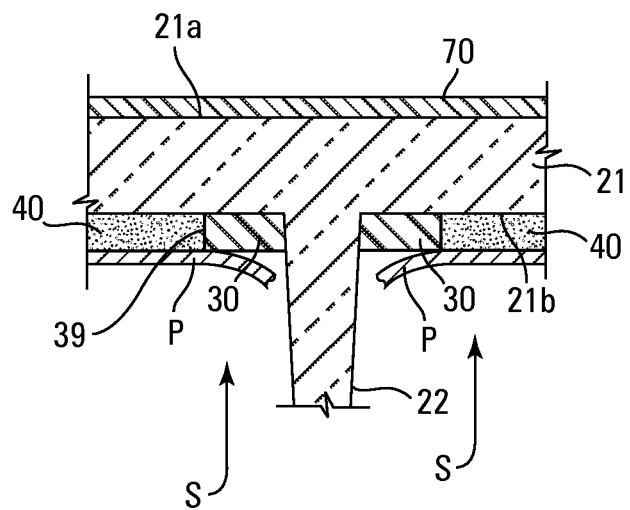
FIG. 8 is a cross-sectional side view of a central portion of the invention depicted in FIG. 6 with the thickness of each layer grossly enlarged to facilitate viewing of the individual layers.

Referring to FIGS. 7 and 8, the probe 10 can be placed into sensing communication with the retention chamber S of a container or package P by pushing the shank 22 of the tack 20 through the lid or sidewall of the container or package P and pressing the adhesive layer 40 on the underside 21b of the head 21 of the tack 20 into sealing engagement with the container or package P. Once the probe 10 is adhered to the container or package P, oxygen is exchanged between the photoluminescent element 30 and the content of the retention chamber S of the container or package P through the opening (unnumbered) in the container or package P created by the shank 22 of the tack 20. Unless the probe 10 is read for several days after being applied to a container or package P, diffusion of oxygen across the head 21 of the tack 20 is statistically insignificant. In those situations where diffusion of oxygen across the head 21 of the tack 20 may become an issue, diffusion can be minimized by constructing the tack 20 from an oxygen impermeable material (i.e., an extremely low oxygen transmission rate (OTR)) or applying a coating of an oxygen impermeable material to the head 21 of the tack 20. Unfortunately, this same option is not available for minimizing diffusion across the layer of pressure-sensitive adhesive 40 as pressure-sensitive adhesives have a fairly high OTR. Hence, in order to minimize diffusion from the sides of the probe 10, the thickness of the pressure-sensitive adhesive layer 40 should be limited (e.g., about 1 to 2 mm) so as to minimize the surface area exposed to the surrounding environment, and a sizable margin 50 provided from the edge(s) 49 of the adhesive layer 40 to the edge(s) 39 of the photoluminescent element 30 (e.g., about 1 to 10 mm) to maximize the width of the adhesive between the surrounding environment and the photoluminescent element 30. The desired effect can generally be achieved with a peripheral margin 50 of between about 1 to 10 mm, most preferably about 2 to 5 mm. A peripheral margin 50 less than about 1 mm does not provide a sufficient delay nor reduction in radial oxygen diffusion through the adhesive layer 40 and into sensing contact with the photoluminescent element 30, while a peripheral margin 50 of greater than about 10 mm increases the expense of the tack 20 without a concomitant improvement in performance.

A release liner 60 is preferably employed over the exposed surface of the adhesive layer 40 to prevent contamination and premature adhesion of probe 10 during storage and handling. A radially extending tab 61 can be provided on the release liner 60 to facilitate removal.

A label 70 can be adhered to the topside 21a of the head 21 of the tack 20 for provided relevant information about the probe 10 such as source, type, phone number for ordering additional probes 10 or obtaining technical support, website address where purchasing and performance details can be obtained, etc. When employed, either (1) The label 70 needs to be transparent or translucent to radiation at the excitation and emission wavelengths of the photoluminescent element 30, or (2) that portion of the label 70 which would overlay the photoluminescent element 30 needs to be removed (e.g., an annular label).

Manufacture

The probe 10 can be conveniently manufactured by (1) obtaining a suitable tack 20, (2) spindling a photoluminescent element 30 (with or without a prepunched hole) onto the underside 21b of the head 21 of the tack 20, (3) applying a layer of pressure-sensitive adhesive 40 onto the underside 21b of the head 21 of the tack 20 before or after the photoluminescent element 30 is spindled onto the tack 20 using conventional coating techniques, (4) spindling a release liner 60 (with or without a prepunched hole) over the exposed surface (unnumbered) of the adhesive layer 40, and (5) optionally applying a label 70 to the topside 21a of the head 21 of the tack 20.

The photoluminescent element 30 can be manufactured by the traditional methods employed for manufacturing such elements 30. Briefly, the element 30 can be conveniently manufactured by (A) preparing a coating cocktail (not shown) which contains the photoluminescent oxygen-sensitive dye 33 and an oxygen-permeable carrier polymer 32 in an organic solvent (not shown) such as ethylacetate, (B) applying the cocktail to the support structure 31, and (C) allowing the cocktail (not shown) to dry, whereby a solid-state thin film oxygen-sensitive photoluminescent element 30 is formed on the support structure 31.

Generally, the concentration of the carrier polymer 32 in the organic solvent (not shown) should be in the range of 0.1 to 20% w/w, with the ratio of dye 33 to polymer 32 in the range of 1:20 to 1:10,000 w/w, preferably 1:50 to 1:5,000 w/w.

Use

The probe 10 can be used to quickly, easily, accurately and reliably measure oxygen concentration within an enclosed space S. Briefly, the probe 10 is used to measure oxygen concentration within an enclosed space S by (A) pushing the shank 22 of the tack 20 through the lid or sidewall of a container or package P defining the enclosed space S until the adhesive layer 40 on the underside 21b of the head 21 of the tack 20 sealingly engages the container or package P, thereby placing the photoluminescent element 30 in sensible communication with the enclosed space S through the opening (unnumbered) in the container or package P created by the shank 22 of the tack 20, (B) allowing the concentration of oxygen in sensible communication with the oxygen-sensitive photoluminescent element 30 to equilibrate with the oxygen concentration in the enclosed space S, and (C) ascertaining oxygen concentration within the enclosed space S by (i) exposing the oxygen-sensitive photoluminescent element 30 to excitation radiation through the head 21 of the tack 20, (ii) measuring radiation emitted by the excited oxygen-sensitive photoluminescent element 30 through the head 21 of the tack 20, and (iii) converting the measured emission to an oxygen concentration based upon a known conversion algorithm. Such conversion algorithms are well know to and readily developable by those with routine skill in the art.

In a similar fashion, the probe 10 can be used to quickly, easily, accurately and reliably monitor changes in oxygen concentration within an enclosed space S. Briefly, the probe 10 is used to monitor changes in oxygen concentration within an enclosed space S by (A) pushing the shank 22 of the tack 20 through the lid or sidewall of a container or package P defining the enclosed space S until the adhesive layer 40 on the underside 21b of the head 21 of the tack 20 sealingly engages the container or package P, thereby placing the photoluminescent element 30 in sensible communication with the enclosed space S through the opening (unnumbered) in the container or package P created by the shank 22 of the tack 20, (B) allowing the concentration of oxygen in sensible communication with the oxygen-sensitive photoluminescent element 30 to equilibrate with the oxygen concentration in the enclosed space S, (C) ascertaining oxygen concentration within the enclosed space S by (i) repeatedly exposing the oxygen-sensitive photoluminescent element 30 to excitation radiation through the head 21 of the tack 20 over time, (ii) measuring radiation emitted by the excited oxygen-sensitive photoluminescent element 30 through the head 21 of the tack 20 after at least some of the exposures, (iii) measuring passage of time during the repeated excitation exposures and emission measurements, and (iv) converting at least some of the measured emission to an oxygen concentration based upon a known conversion algorithm, and (D) reporting at least one of (i) at least two ascertained oxygen concentrations and the time interval between those reported concentrations, or (ii) a rate of change in oxygen concentration within the enclosed space S calculated from data obtained in step (C). Again, conversion algorithms used to convert the measured emissions to an oxygen concentration are well know to and readily developable by those with routine skill in the art.

The radiation emitted by the excited probe 10 can be measured in terms of intensity and/or lifetime (rate of decay, phase shift or anisotropy), with measurement of lifetime generally preferred as a more accurate and reliable measurement technique when seeking to establish oxygen concentration via measurement of the extent to which the dye 33 in the photoluminescent element 30 has been quenched by oxygen.

We claim:

1. A photoluminescent oxygen probe comprising:
   (a) a tack with a head and a shank extending longitudinally from an underside of the head,
   (b) a layer of a pressure-sensitive adhesive on the underside of the head, and
   (c) an oxygen-sensitive photoluminescent element on the underside of the head.

2. The probe of claim 1 wherein the layer of adhesive is positioned intermediate the head of the tack and the oxygen-sensitive photoluminescent element.

3. The probe of claim 1 wherein the oxygen-sensitive photoluminescent element includes at least an oxygen-sensitive photoluminescent dye embedded within an oxygen-permeable hydrophobic polymer carrier.

4. The probe of claim 1 wherein the oxygen-sensitive photoluminescent element includes at least a support structure coated with an oxygen-sensitive photoluminescent dye embedded within an oxygen-permeable hydrophobic polymer carrier.

5. The probe of claim 4 wherein the oxygen-sensitive photoluminescent dye is a tetrabenzoporphyrin.

6. The probe of claim 1 wherein the layer of pressure-sensitive adhesive is less than 2 mm thick.

7. The probe of claim 6 wherein (i) the shank defines a longitudinal axis, (ii) the layer of pressure sensitive adhesive has a peripheral edge, (iii) the oxygen-sensitive photoluminescent element has a peripheral edge, and (iv) the adhesive layer extends radially from the longitudinal axis of the shank at least 2 mm beyond the peripheral edge of the oxygen-sensitive photoluminescent element around the entire periphery of the oxygen-sensitive photoluminescent element.

8. A method for measuring the oxygen concentration within a space enclose by a structure, comprising the steps of:
   (a) obtaining a photoluminescent oxygen probe according to claim 7,
   (b) puncturing the structure with the probe's shank,
   (c) adhering the underside of the probe's head to an exterior surface of the structure so as to sealingly surround the puncture, thereby placing the oxygen-sensitive photoluminescent element on the underside of the probe's head into sensible communication with the enclosed space through the puncture,
   (d) allowing an oxygen concentration in sensible communication with the oxygen-sensitive photoluminescent element to equilibrate with an oxygen concentration within the enclosed space, and
   (e) ascertaining an oxygen concentration within the enclosed space by: (i) exposing the oxygen-sensitive photoluminescent element on the underside of the probe's head to excitation radiation through the probe's head, (ii) measuring radiation emitted by the excited oxygen-sensitive photoluminescent element, and (iii) converting the measured emission to an oxygen concentration based upon a known conversion algorithm.

9. A method for monitoring changes in oxygen concentration within a space enclosed by a membrane, comprising the steps of:
   (a) obtaining a photoluminescent oxygen probe according to claim 7,
   (b) puncturing the membrane with the probe's shank,
   (c) adhering the underside of the probe's head to an exterior surface of the membrane so as to sealingly surround the puncture, thereby placing the oxygen-sensitive photoluminescent element on the underside of the probe's head into sensible communication with the enclosed space through the puncture,
   (d) allowing an oxygen concentration in sensible communication with the oxygen-sensitive photoluminescent element to equilibrate with an oxygen concentration within the enclosed space,
   (e) ascertaining an oxygen concentration within the enclosed space over time by: (i) repeatedly exposing the equilibrated oxygen-sensitive photoluminescent element on the underside of the probe's head to excitation radiation through the probe's head over time, (ii) measuring radiation emitted by the excited equilibrated oxygen-sensitive photoluminescent element after at least some of the exposures, (iii) measuring passage of time during the repeated excitation exposures and emission measurements, and (iv) converting at least some of the measured emissions to an oxygen concentration based upon a known conversion algorithm, and
   (f) reporting at least one of (i) at least two ascertained oxygen concentrations and a time interval between those reported concentrations, and (ii) a rate of change in oxygen concentration within the enclosed space calculated from data obtained in step (e).

10. The probe of claim 1 wherein the layer of pressure-sensitive adhesive is less than 1.5 mm thick.

11. The probe of claim 1 wherein (i) the shank defines a longitudinal axis, (ii) the layer of pressure sensitive adhesive has a peripheral edge, (iii) the oxygen-sensitive photoluminescent element has a peripheral edge, and (iv) the adhesive layer extends radially from the longitudinal axis of the shank at least 4 mm beyond the peripheral edge of the oxygen-sensitive photoluminescent element around the entire periphery of the oxygen-sensitive photoluminescent element.

12. A method for measuring the oxygen concentration within a space enclosed by a structure, comprising the steps of:
   (a) obtaining a photoluminescent oxygen probe according to claim 1,
   (b) puncturing the structure with the probe's shank,
   (c) adhering the underside of the probe's head to an exterior surface of the structure so as to sealingly surround the puncture, thereby placing the oxygen-sensitive photoluminescent element on the underside of the probe's head into sensible communication with the enclosed space through the puncture,
   (d) allowing an oxygen concentration in sensible communication with the oxygen-sensitive photoluminescent element to equilibrate with an oxygen concentration within the enclosed space, and
   (e) ascertaining an oxygen concentration within the enclosed space by: (i) exposing the oxygen-sensitive photoluminescent element on the underside of the probe's head to excitation radiation through the probe's head, (ii) measuring radiation emitted by the excited oxygen-sensitive photoluminescent element, and (iii) converting the measured emission to an oxygen concentration based upon a known conversion algorithm.

13. The method of claim 12 wherein the space is a retention chamber of a hermetically sealed package containing an oxygen labile pharmaceutical or foodstuff.

14. A method for monitoring changes in oxygen concentration within a space enclosed by a membrane, comprising the steps of:
   (a) obtaining a photoluminescent oxygen probe according to claim 1,
   (b) puncturing the membrane with the probe's shank, (c) adhering the underside of the probe's head to an exterior surface of the membrane so as to sealingly surround the puncture, thereby placing the oxygen-sensitive photoluminescent element on the underside of the probe's head into sensible communication with the enclosed space through the puncture, (d) allowing an oxygen concentration in sensible communication with the oxygen-sensitive photoluminescent element to equilibrate with an oxygen concentration within the enclosed space, (e) ascertaining an oxygen concentration within the enclosed space over time by: (i) repeatedly exposing the equilibrated oxygen-sensitive photoluminescent element on the underside of the probe's head to excitation radiation through the probe's head over time, (ii) measuring radiation emitted by the excited equilibrated oxygen-sensitive photoluminescent element after at least some of the exposures, (iii) measuring passage of time during the repeated excitation exposures and emission measurements, and (iv) converting at least some of the measured emissions to an oxygen concentration based upon a known conversion algorithm, and (f) reporting at least one of (i) at least two ascertained oxygen concentrations and a time interval between those reported concentrations, and (ii) a rate of change in oxygen concentration within the enclosed space calculated from data obtained in step (e).

15. The method of claim 14 wherein the space is a retention chamber of a hermetically sealed package containing an oxygen labile pharmaceutical or foodstuff.

\* \* \* \* \*